(12) United States Patent
Martinez

(10) Patent No.: US 8,217,202 B2
(45) Date of Patent: Jul. 10, 2012

(54) SINGLE CARBON PRECURSOR SYNTHONS

(75) Inventor: Rodolfo A. Martinez, Santa Fe, NM (US)

(73) Assignee: New Mexico Highlands University, Las Vegas, NM (US)

( * ) Notice: Subject to any disclaimer, the term of this patent is extended or adjusted under 35 U.S.C. 154(b) by 529 days.

(21) Appl. No.: 12/098,135

(22) Filed: Apr. 4, 2008

(65) Prior Publication Data

US 2008/0255370 A1    Oct. 16, 2008

Related U.S. Application Data

(60) Provisional application No. 60/923,107, filed on Apr. 11, 2007, provisional application No. 60/948,359, filed on Jul. 6, 2007.

(51) Int. Cl.
*C07C 323/19* (2006.01)

(52) U.S. Cl. ........................................................ 568/39

(58) Field of Classification Search ..................... 568/39
See application file for complete search history.

(56) References Cited

U.S. PATENT DOCUMENTS

| 6,713,044 B2 * | 3/2004 | Martinez et al. ............. 424/1.81 |
| 2003/0204108 A1 | 10/2003 | Martinez et al. |
| 2006/0160813 A1 | 7/2006 | Sterk |
| 2006/0178534 A1 | 8/2006 | Martinez et al. |
| 2007/0004929 A1 * | 1/2007 | Martinez et al. ................ 556/87 |

OTHER PUBLICATIONS

Lattre, CAS Accession No. 1913:9276.*
PCT—Notification of Transmittal of the International Search Report and the Written Opinion of the International Searching Authority, or the Declaration, Date of Mailing: Jul. 7, 2008.

* cited by examiner

*Primary Examiner* — Joseph Kosack
(74) *Attorney, Agent, or Firm* — Melissa Asfahani; Luis M. Ortiz; Kermit D. Lopez

(57) ABSTRACT

The chemistry of [$^{13}$C]methyl phenyl sulfide is exploited to produce new isotopically labeled precursors that allow for the facile assembly of a wide range of labeled molecules from simple and relatively inexpensive starting materials. These compounds are applicable to a variety of research areas such as quantum computing, metabolism and materials science.

1 Claim, 13 Drawing Sheets

X = H or ²H

Z = Cl, Br, I

R₁ - R₅ = H or Alkyl or O-Alkyl or S-Alkyl
or Cl, Br, I

X = H or ²H

Z = Cl, Br, I

R₁ - R₅ = H or Alkyl or O-Alkyl or S-Alkyl
or Cl, Br, I

X = H or ²H
Z = Cl, Br, I

R₁ - R₅ = H or Alkyl or O-Alkyl or S-Alkyl
or Cl, Br, I

X = H or ²H
Z = Cl, Br, I

R₁ - R₅ = H or Alkyl or O-Alkyl or S-Alkyl
or Cl, Br, I

X = H or ²H

Z = Cl, Br, I

R₁ - R₅ = H or Alkyl or O-Alkyl or S-Alkyl
or Cl, Br, I

X = H or ²H

Z = Cl, Br, I

R₁ - R₅ = H or Alkyl or O-Alkyl or S-Alkyl
or Cl, Br, I

1-[(Arylthio)[$^{13}$C]methyl]-2,5-Pyrrolidinediones

1-[(Arylthio)[$^{13}$C]methyl]-2,5-[$^{15}$N]Pyrrolidinediones

1-[(Arylthio)[$^{13}$C]methyl]-phthalimides

1-[(Arylthio)[$^{13}$C]methyl]-[$^{15}$N]phthalimides

SINGLE CARBON PRECURSOR SYNTHONS

CROSS REFERENCE TO RELATED APPLICATIONS

This patent application claims the priority and benefit of two U.S. Provisional Patent Applications the first being No. 60/923,107 filed Apr. 11, 2007 entitled "Carbon Labeled, Isotopically Labeled C13 Molecules and also deuterium Labeled Molecules Based on the Chemistry of C13 Methyl Phenyl Sulfide" and the second being No. 60/948,359 filed Jul. 6, 2007 and titled "Synthesis of Isotopically Tagged Synons". Both 60/923,107 and 60/948,359 are herein incorporated by reference.

TECHNICAL FIELD

The present invention relates to labeled compounds and more particularly to compounds derived from isotopically enriched Alkoxy[$^{13}$C]methyl phenyl sulfone or Alkoxy[$^{14}$C] methyl phenyl sulfone. As such, the isotopic tags can be carbon-13 or carbon-14.

BACKGROUND OF THE INVENTION

Phenyl sulfones are extremely useful for the synthesis of many important biochemicals and pharmaceuticals. Additionally, the use of stable isotopes has long been considered to be a promising tool in biomedical diagnosis. Furthermore, the past two decades have seen a tremendous leap forward in the development of very sophisticated instrumentation for the detection of disease and for probing biological structure and function. In conjunction with this a need for very complicated isotopically labeled materials has been on the increase.

Another area of application has become critical after the "9/11" tragedies. The use of stable isotopes in molecules (metabolites) for the rapid detection of threat agents (chemical and biological) is now in large demand. Current isotopic labeling precursors and techniques, however, have made this a very daunting task.

In order to meet the urgent and growing demand, high purity isotopically labeled compounds are needed.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

It is therefore an aspect of the embodiments to exploit the chemistry of [$^{13}$C]methyl phenyl sulfide to produce new isotopically labeled precursors that allow for the facile assembly of a wide range of labeled molecules from simple and relatively inexpensive starting materials. These compounds are applicable to a variety of research areas such as quantum computing, metabolism and materials science.

BRIEF DESCRIPTION OF THE DRAWINGS

The accompanying figures, in which like reference numerals refer to identical or functionally similar elements throughout the separate views and which are incorporated in and form a part of the specification, further illustrate aspects of the embodiments and, together with the background, brief summary, and detailed description serve to explain the principles of the embodiments.

DETAILED DESCRIPTION

Figure 1:
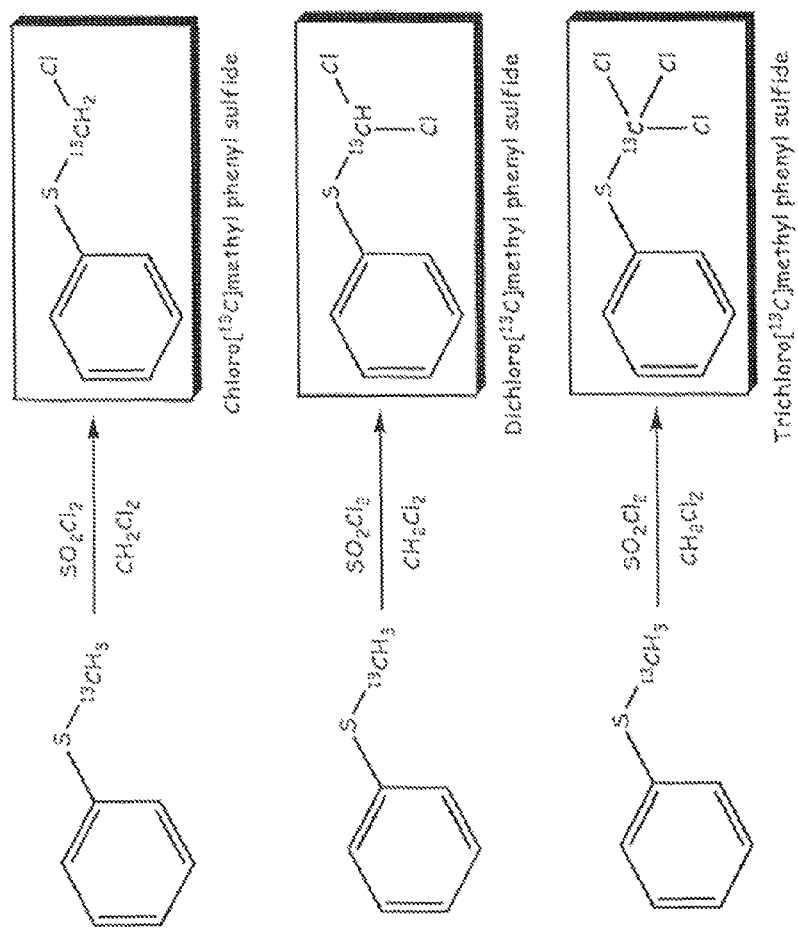
FIG. 1 illustrates producing Chloro[$^{13}$C]methyl phenyl sulfide, dichloro[$^{13}$C]methyl phenyl sulfide and trichloro [$^{13}$C]methyl phenyl sulfide in accordance with aspects of the embodiments.
Figure 2:
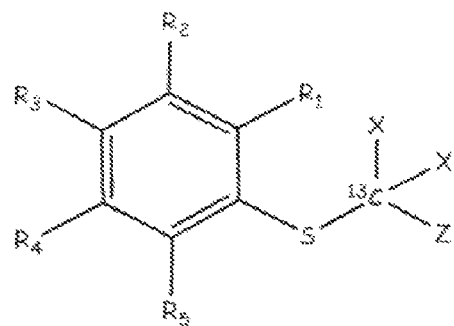
FIG. 2 illustrates the general structures of Chloro[$^{13}$C] methyl phenyl sulfide, dichloro[$^{13}$C]methyl phenyl sulfide, trichloro[$^{13}$C]methyl phenyl sulfide and other closely related compounds in accordance with aspects of the embodiments.
Figure 2:
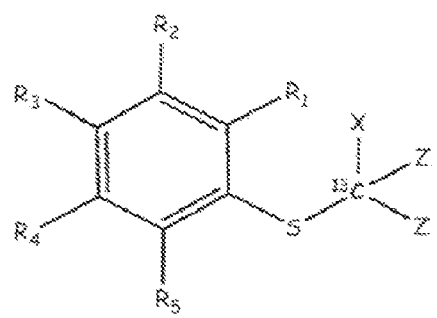
Figure 2:
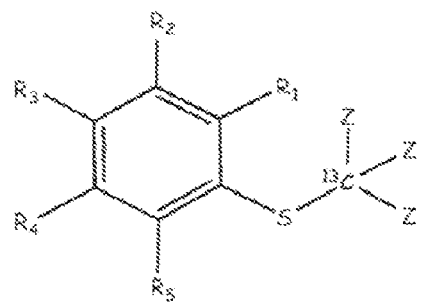
Figure 3:
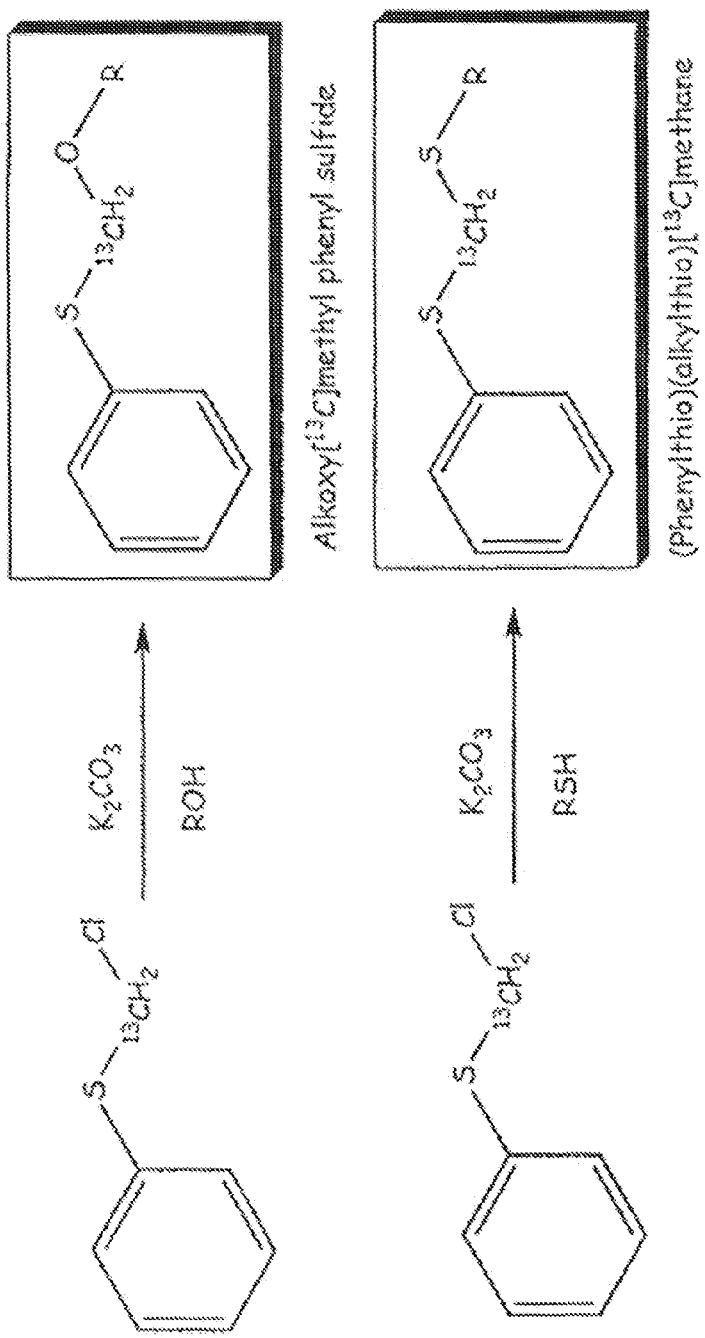
FIG. 3 illustrates producing Alkoxy[$^{13}$C]methyl Phenyl Sulfide and (Phenylthio)(alkylthio)[$^{13}$C]methane in accordance with aspects of the embodiments.
Figure 4:
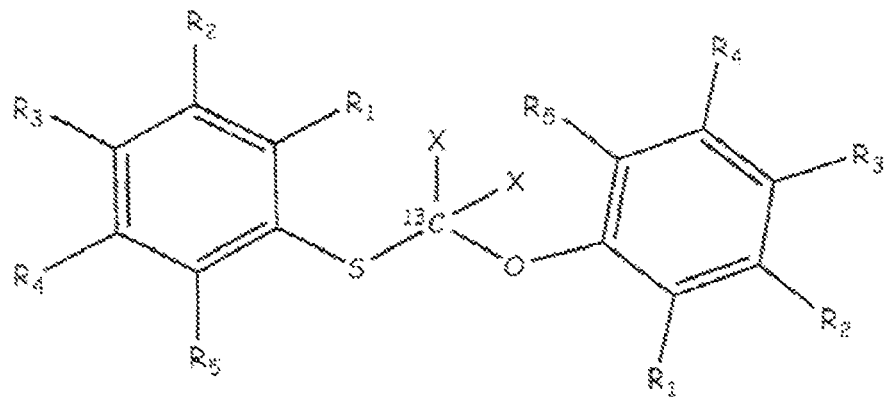
FIG. 4 illustrates the general structures of Alkoxy[$^{13}$C] methyl Phenyl Sulfide, (Phenylthio)(alkylthio)[$^{13}$C]methane and other closely related compounds in accordance with aspects of the embodiments.
Figure 4:
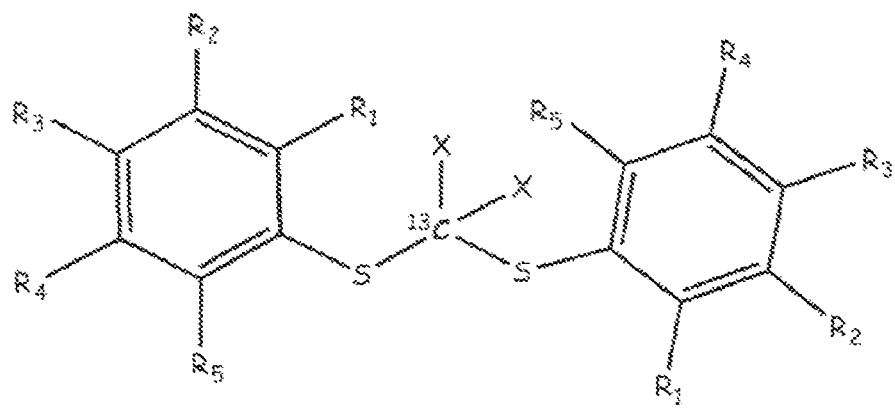
Figure 5:
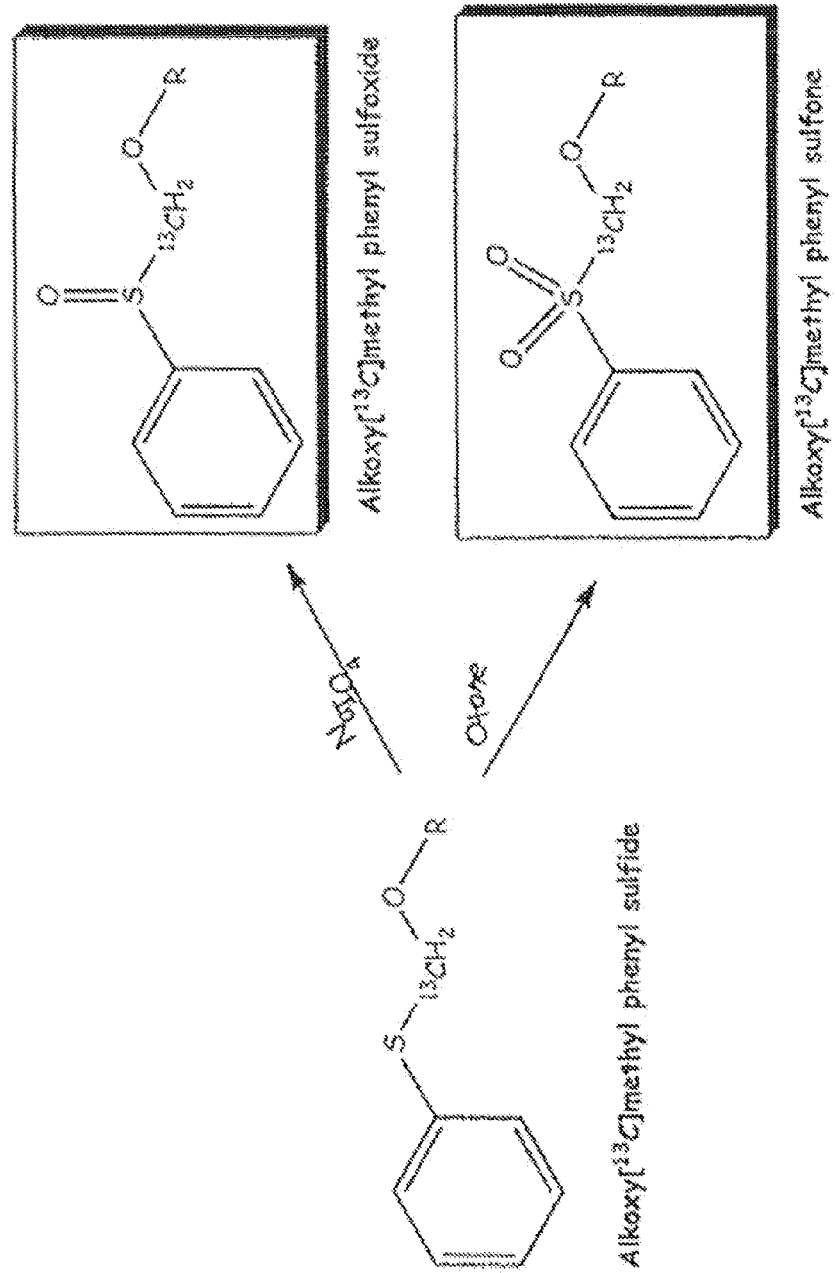
FIG. 5 illustrates the oxidation of alkoxy[$^{13}$C]methyl phenyl sulfide in accordance with aspects of the embodiments.
Figure 6:
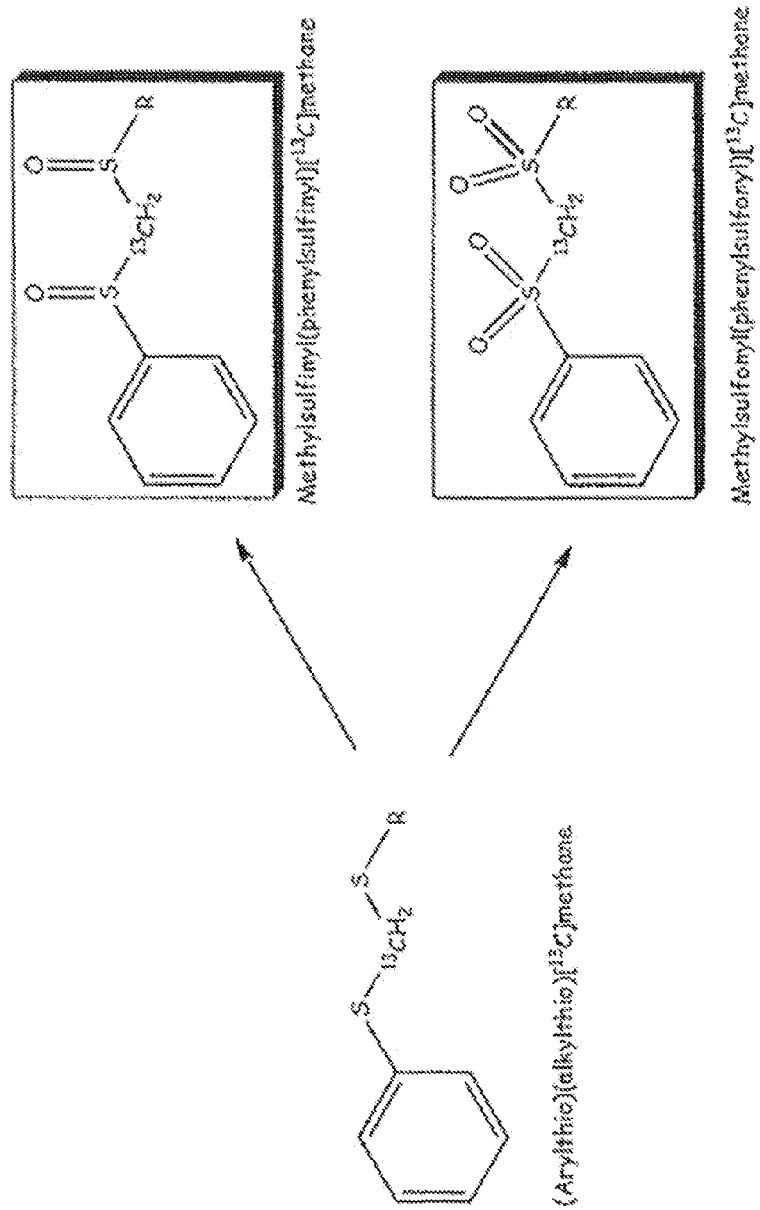
FIG. 6 illustrates the oxidation of (Arylthio)(alkylthio) [$^{13}$C]methane in accordance with aspects of the embodiments.
Figure 7A:
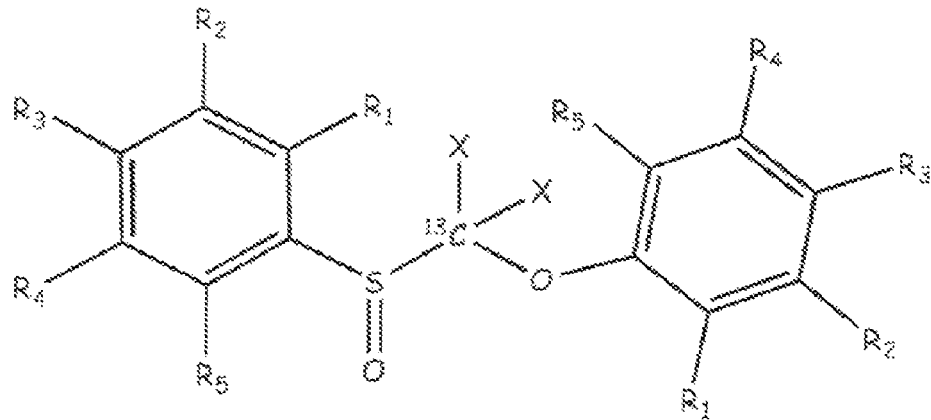
FIG. 7 illustrates the general structures of alkoxy[$^{13}$C] methyl phenyl sulfide, (Arylthio)(alkylthio)[$^{13}$C]methane and other closely related compounds in accordance with aspects of the embodiments.
Figure 7A:
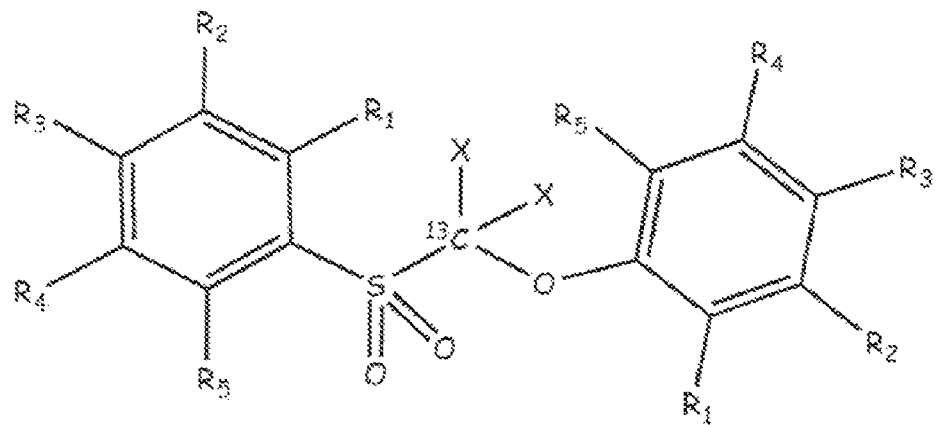
Figure 7B:
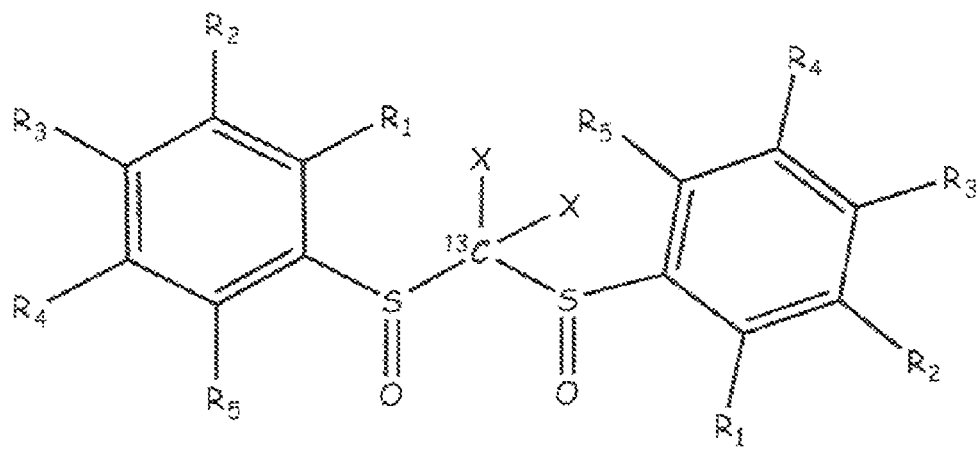
Figure 7B:
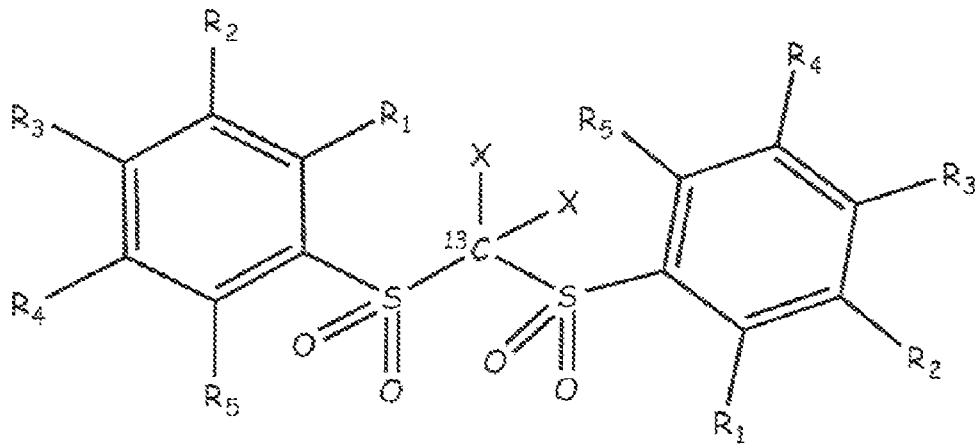
Figure 8:
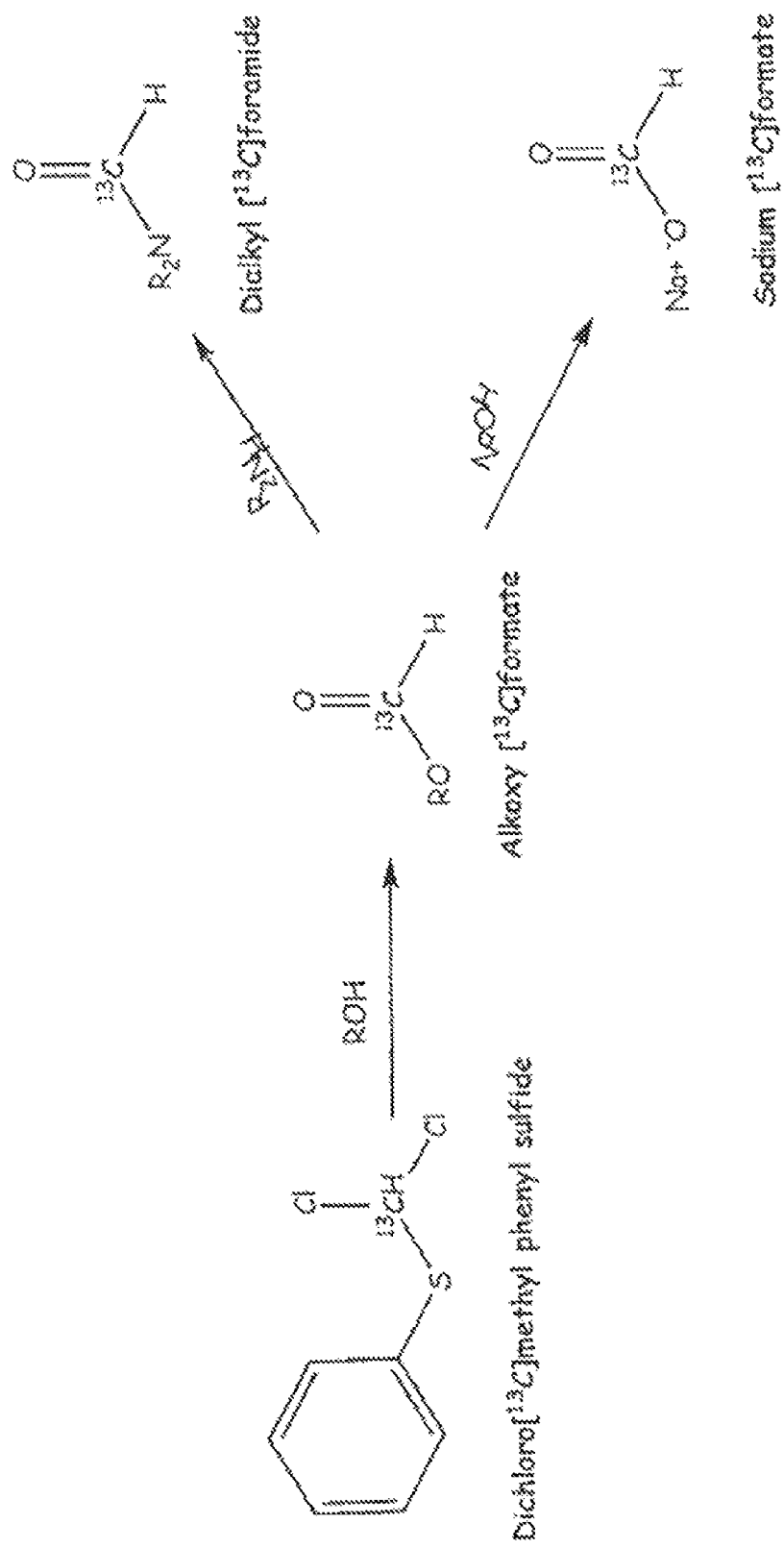
FIG. 8 illustrates the reactions of dichloro[$^{13}$C]ethyl phenyl sulfide in accordance with aspects of the embodiments.
Figure 9:
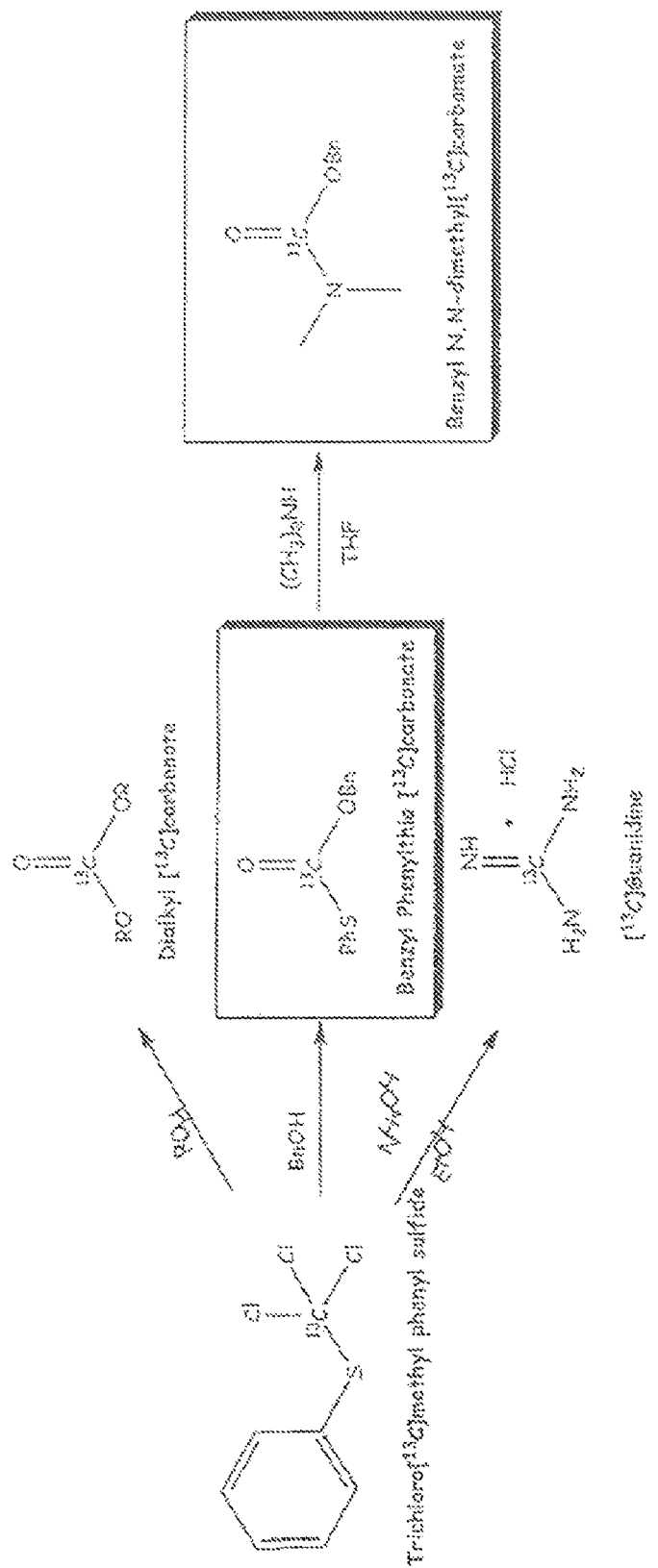
FIG. 9 illustrates the reactions of trichloro[$^{13}$C]methyl phenyl sulfide in accordance with aspects of the embodiments.
Figure 10:
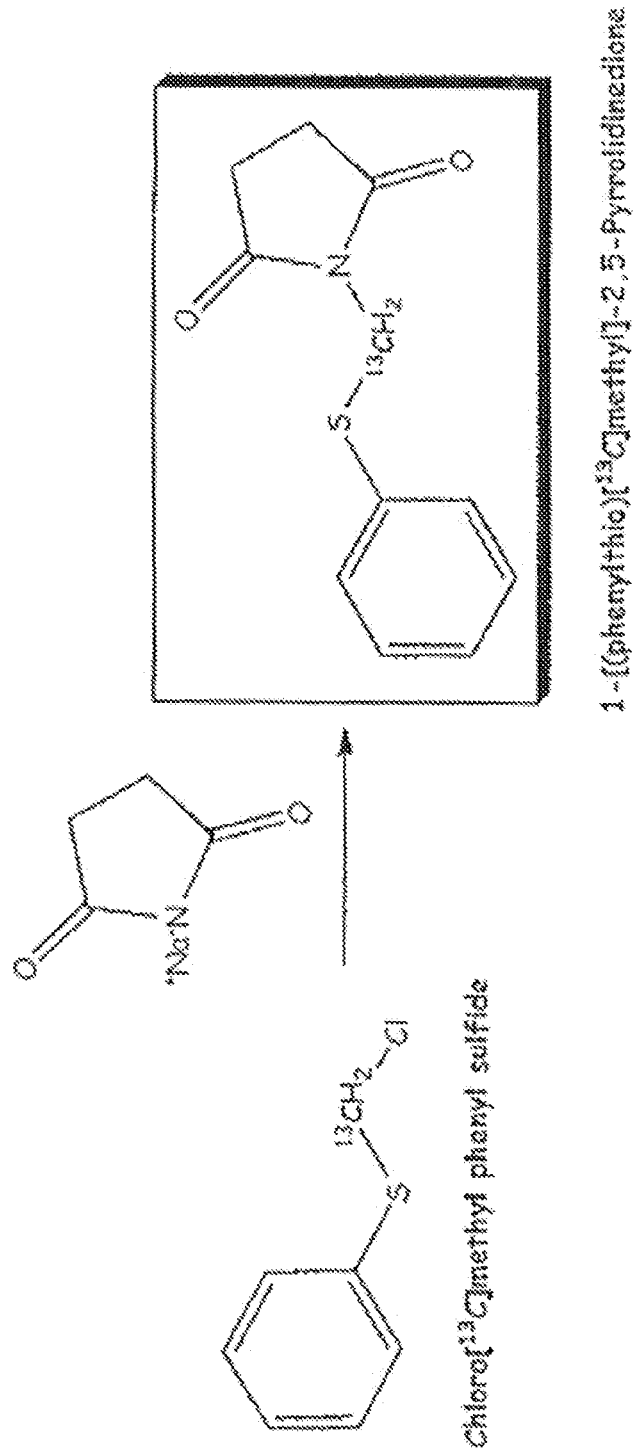
FIG. 10 illustrates the synthesis of 1-[(phenylthio)[$^{13}$C] methyl]-2,5-Pyrrolidinedione in accordance with aspects of the embodiments.
Figure 11A:
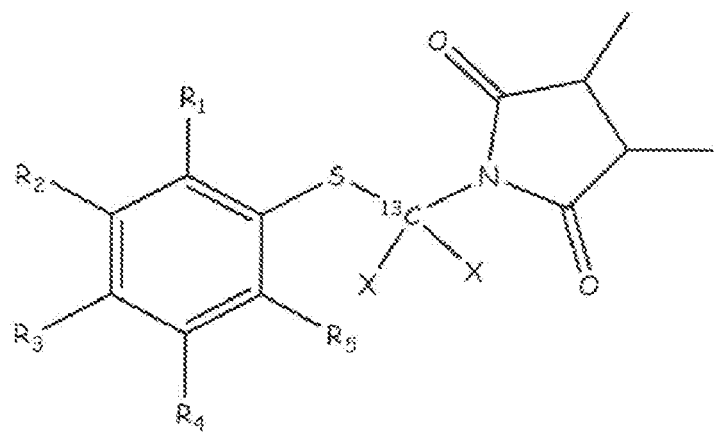
FIG. 11 illustrates the general structures of 1-[(phenylthio) [$^{13}$C]methyl]-2,5-Pyrrolidinedione and other closely related compounds in accordance with aspects of the embodiments.
Figure 11A:
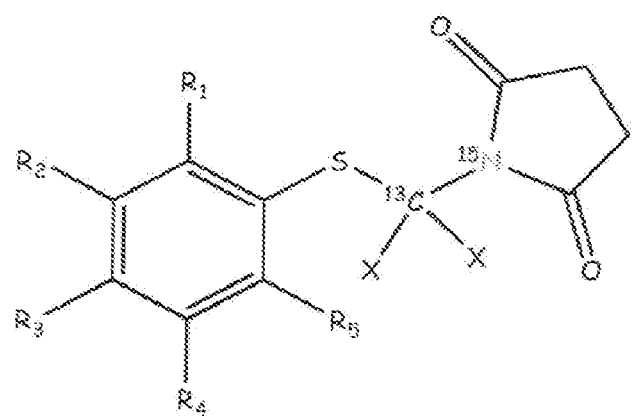
Figure 11B:
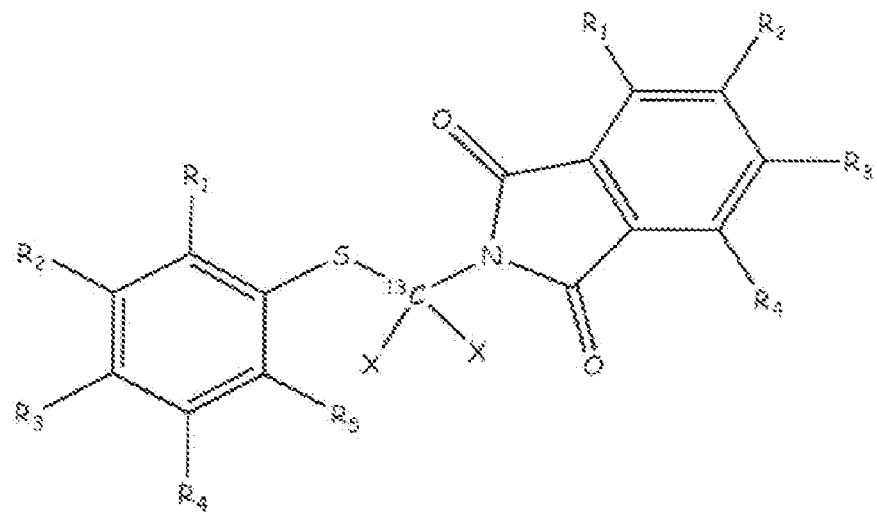
Figure 11B:
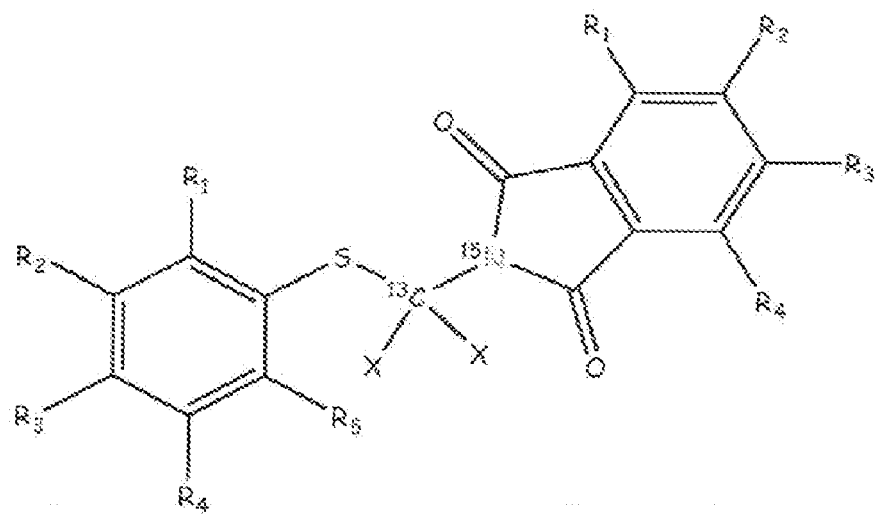

The following description contains a series of examples wherein previously known labeled compounds are processed to yield highly pure labeled compounds that are not previously known.

Synthesis of dichloro[$^{13}$C]methyl phenyl sulfide

A sample of [$^{13}$C]-Methyl phenyl sulfide (91.3%, 6.3 g, 0.046 mol, 1 equivalent) was dissolved in thiophene-free benzene (50 mL) in a 250 mL round bottom flask, flushed with argon and was cooled using an ice-water bath. Once the benzene began to freeze, N-chlorosuccinimide (13.08 g, 0.098 mol, 2.1 eq) was added in a single portion while stirring rapidly. The reaction mixture was permitted to warm to room temperature slowly as the ice bath melted, while stirring under argon. After 24 hours, the reaction was found to be complete by $^{13}$C NMR by taking an aliquot from the reaction mixture, dissolving it into CDCl$_3$, and monitoring the disappearance of [$^{13}$C]-methyl phenyl sulfide (δ=16.9 ppm) and subsequent appearance of the desired dichloro-[$^{13}$C]-methyl phenyl sulfide (δ=76.0 ppm). The reaction mixture was then filtered to remove succinimide, the solids were washed with benzene and volatiles were removed by vacuum. The resulting oil contained some succinimide and this oil and precipitate were partitioned between water and dichloromethane in order to remove the remaining succinimide. The organic layer was washed with water (100 mL, 2×) filtered through cotton, and volatiles again removed by vacuum to give a quantitative yield of clear pale yellow liquid which was used without further purification.

The spectra data are as follows:
$^1$H NMR (CDCl$_3$, 300 MHz): δ=7.45-7.59 (m, 3H), 7.79 (d, 2H)
$^{13}$C NMR (CDCl$_3$, 75 MHz): δ=98.9 ($^{13}$CCl$_3$), 129.5 (ArC-3), 130.9 (d, $^2J_{CC}$=3.3 Hz, ArC-1), 131.9 (d, $^3J_{CC}$=2.2 Hz, ArC-2), 137.5 (ArC-4)

Synthesis of trichloro[$^{13}$C]methyl phenyl sulfide

A sample of [$^{13}$C]-Methyl phenyl sulfide (91.3%, 28.8 g, 0.210 mol. 1 equivalent) was dissolved in thiophene-free benzene (350 mL) in a two liter Morton Flask, flushed with argon and was cooled using an ice-water bath. Once the benzene began to freeze, N-chlorosuccinimide (103 g, 0.771 mol. 3.7 eq) was added over a period of 7 minutes, via spatula as quickly as possible. The reaction mixture was gradually allowed to come to room temperature and stirred for 24 hours under argon. After 24 hours, the reaction was found to be complete by $^{13}$ NMR by taking an aliquot from the reaction mixture, dissolving it into CDCl$_3$, and monitoring the disappearance of [$^{13}$C]-methyl phenyl sulfide (δ=16.9 ppm) and subsequent appearance of the desired trichloro-[$^{13}$C]-methyl phenyl sulfide (δ=98.9 ppm). The reaction mixture was then filtered to remove succinimide, the solids were washed with benzene and volatiles were removed by vacuum. The resulting oil contained some succinimide and this oil and precipitate were partitioned between water and dichloromethane in order to remove the remaining succinimide. The organic layer was washed with water (300 mL, 2×) filtered through cotton, and volatiles again removed by vacuum to give a quantitative yield of colorless, low-melting crystalline solid that was suitable for single crystal x-ray analysis. A single crystal x-ray structure was determined for this compound.

The spectra data are as follows:
$^1$H NMR (CDCl$_3$, 300 MHz): δ=7.45-7.59 (m, 3H), 7.79 (d, 2H)
$^{13}$C NMR (CD)Cl$_3$, 75 MHz): δ 98.9 ($^{13}$CCl$_3$), 129.5 (ArC-3), 130.9 (d, $^2J_{CC}$=3.3 Hz, ArC-1), 131.9 (d, $^3J_{CC}$=2.2 Hz, ArC-2), 137.5 (ArC-4)

Synthesis of Ethoxy[$^{13}$C]methyl phenyl sulfide

Chloro[$^{13}$C]methyl phenyl sulfide (12.0 g, 0.075 mol) and ethyl alcohol (120 mL, 100%) were placed in a 250 mL round bottom flask equipped with a magnetic stir bar and a rubber septum. This mixture was sonicated at 40° C. for 6 hrs and then allowed to stir overnight at room temperature without sonication. After this period, $^{13}$CNMR analysis showed the complete disappearance of the starting material at 51 ppm and the quantitative formation of the desired product at 74 ppm. The reaction mixture was then transferred to a separatory funnel containing dichloromethane (120 mL) and DI water (100 mL). The organic layer was separated, dried over anhydrous sodium sulfate, filtered and then concentrated in vacuo to afford 12.46 g (98.2%) of the titled compound as a pale yellow fluid. The crude product was sufficiently pure and was used in the next reaction without further purification.

The spectra data are as follows:
$^1$HNMR (300 MHz in CDCl$_3$ with 0.03% TMS) δ: 7.48-7.18 (5H, m), δ: 5.23, 4.70 (2H, d J 158.1) δ: 3.68, 3.67, 3.66, 3.65, 3.63, 3.62, 3.61, 3.60 (2H, qd J 6.98, 3.67) δ: 1.23, 1.19, 1.18 (3H, t J 6.99). $^{13}$CNMR (75 MHz in CDCl$_3$) δ: 136.398, 130.23, 129.00, 126.71, 74.70, 63.93, and 15.80; Mass spectra m/e 169 (M+.), 124, 109, and 60.

Synthesis of ethoxy[$^{13}$C]methyl phenyl sulfoxide

A sample of ethoxy[$^{13}$C]methyl phenyl sulfide (10 g, 0.059 moles) was dissolved in ethanol (100 mL) and hydrogen peroxide (30% by wt., 13.4 mL, 0.118 moles) was added. The reaction was stirred for 24 hours at ambient temperature. The product was extracted with dichloromethane (3×100 mL). The dichloromethane layer was washed with water (3×100 mL) until the aqueous portion tested negative to KI starch paper. The product was suitable for use in subsequent reactions without purification.

The spectra data are as follows:
$^1$HNMR (300 MHz in CDCl$_3$ with 0.03% TMS)/δ: 7.95-7.55 (m 5H), δ: 4.81, 4.30 (d J 154.43 $^{13}$CH$_2$); δ: 3.93, 3.91, 3.89, 3.90, 3.89, 3.87, 3.86, 3.85, 3.84 (qd J 6.99, 3.31 — OCH$_2$) δ: 1.21, 1.19, 1.16 (t J 6.99). $^{13}$CNMR (75 MHz in CDCl$_3$) δ: 134.99, 134.20, 129.36, 128.97 δ: 86.43 (s, $^{13}$CH$_2$) δ: 69.53, (—OCH$_2$), and 15.20 (CH$_3$).

Synthesis of ethoxy[$^{13}$C]methyl phenyl sulfoxide

An oxone solution (prepared by dissolving 163.69 g of oxone in 720 ml deionized water) was added to an ice-cooled solution of ethoxy[$^{13}$C]-methylphenyl sulfide (16.0 g, 0.095 mol) in ethyl acetate-ethanol (1:1, 150 mL). This reaction mixture was allowed to stir at 0° C. for 30 mins and $^{13}$CNMR in CDCl$_3$ at that point showed a quantitative formation of the desired product peak at 86 ppm. The reaction mixture was poured into a 2-L separatory funnel containing dichloromethane (300 mL) and deionized water (350 mL). The organic layer was separated and washed with deionized water (3×150 mL). The combined organic layers were dried over anhydrous sodium sulfate, filtered and then concentrated in vacuo to afford 18.4 g, (96.7%) of the titled compound as pale yellow fluid pure enough for the next reaction.

The spectra data are as follows:
$^1$HNMR (300 MHz in CDCl$_3$ with 0.03% TMS)/δ: 7.95-7.55 (m 5H), δ: 4.81, 4.30 (d J 154.43 $^{13}$CH$_2$); δ: 3.93, 3.91, 3.89, 3.90, 3.89, 3.87, 3.86, 3.85, 3.84 (qd J 6.99, 3.31 — OCH$_2$) δ: 1.21, 1.19, 1.16 (t J 6.99). $^{13}$CNMR (75 MHz in CDCl$_3$) δ: 134.99, 134.20, 129.36, 128.97 δ: 86.43 (s, $^{13}$CH$_2$) δ: 69.53, (—OCH$_2$), and 15.20 (CH$_3$).

Synthesis of ethyl-[$^{13}$C]-formate

Dichloro-[$^{13}$C]-methyl phenyl sulfide (20.2 g, 0.104 mol, 1 equivalent) was dissolved in ethanol (absolute, 200 mL) in a 1 L round bottom flask. The reaction vessel was loosely sealed with a polyethylene cap and permitted to stir at room temperature. After five days, the reaction was found to be complete by $^{13}$C NMR by taking an aliquot from the reaction solution, dissolving it into CDCl$_3$, and monitoring the disappearance (to within 2% remaining) of dichloro-[$^{13}$C]-methyl phenyl sulfide (δ=76.0 ppm) and subsequent appearance of the desired ethyl-[$^{13}$C]-formate (δ=161.0 ppm). The reaction solution was then washed with aqueous saturated sodium bicarbonate (200 mL, 2×). The layers were separated and the organic layer was washed with 0.1N aqueous sodium hydroxide (200 mL, 1×). The layers were separated and the organic layer was then distilled using a simple distillation apparatus to yield a colorless liquid which was used without further purification.

Synthesis of Diethyl[$^{13}$C]carbonate

Trichloro-[$^{13}$C]-Methyl phenyl sulfide (7.7 g, 0.0333 mol, 1 equivalent) was dissolved in ethanol (absolute, 77 mL) in a 500 mL round bottom flask. The reaction solution was then stirred at room temperature. After six days the reaction was determined to be 85% complete by $^{13}$C NMR by taking an aliquot from the reaction solution, dissolving it into CDCl$_3$, and monitoring the disappearance of trichloro-[$^{13}$C]-methyl phenyl sulfide (δ=98.9 ppm) and subsequent appearance of the desired diethyl-[$^{13}$C]-carbonate (δ=155.2 ppm). The reaction was then placed in a warming bath (45° C.). After an additional 24 hours, the reaction was found to be complete by $^{13}$C NMR using the method described above. The reaction solution was poured into dichloromethane (80 mL) and then washed with aqueous saturated sodium bicarbonate (80 mL). The layers were separated and the organic layer was then washed with 0.1N aqueous sodium hydroxide (150 mL 2x). At this time, $^{13}$C NMR showed no ethanol or thiophenol in the product. The organic layer was then placed onto a rotary evaporator and dichloromethane was removed (P=150 torr, T=25° C.) to yield a colorless liquid that still contained 50% dichloromethane.

Synthesis of [$^{13}$C]guanidine hydrochloride

Ethanol (absolute, 230 mL) was placed into a 1 L round bottom flask with a stir bar. The round bottom flask was then attached to an argon manifold fitted with an oil bubbler in order to maintain slight positive pressure. The round bottom flask was then placed into a methanol bath equipped with a Cryocool immersion chiller. The bath was cooled to −80° C. while maintaining positive pressure on the inert gas manifold, as determined by the oil bubbler. Once the desired temperature was attained, the argon line was disconnected and a fritted glass tube connected to an anhydrous ammonia tank was introduced below the surface of the cold ethanol. Ammonia was dissolved in the cold ethanol by bubbling it through the fritted glass for one-half hour while stirring. The fritted glass tube was then removed from the flask. The reaction vessel was reattached to the argon line, removed from the cold methanol bath and permitted to warm gradually. Once the temperature had reached −15° C. (checked by IR thermometer) ammonium hydroxide (29.9% aqueous sol'n, 60 mL, to make 20% water by volume) was added to the ethanolic solution of ammonia while stirring. Trichloro-[$^{13}$C]-methyl phenyl sulfide (21.81 g, 0.0954 mol, 1 equivalent) was dissolved in dichloromethane (60 mL) in order to aid its solubility in the cold polar solution. When the internal temperature had raised to −5° C. the trichloro-[$^{13}$C]-methyl phenyl sulfide solution was added at once via syringe to the stirring ammonia solution. The reaction mixture was allowed to come to room temperature and stirred for three days under argon. After three days, the solution had turned dark red, and the reaction was found to be complete by $^{13}$C NMR by taking an aliquot from the reaction mixture, partitioning it between D$_2$O and CDCl$_3$, and monitoring the disappearance trichloro-[$^{13}$C]-methyl phenyl sulfide ($\delta$=98.9 ppm relative to CDCl$_3$) in the organic layer and subsequent appearance of the desired guanidine-$^{13}$C hydrochloride ($\delta$=158 ppm relative to ethanol).

In order to remove excess ammonia, argon was bubbled through the rapidly stirring solution using a Pasteur pipette attached to the manifold in order to deliver the stream of argon. All volatiles were removed by rotary evaporator followed by hi-vac to yield a dark brown/black solid. The solid was partitioned between water (100 mL) and dichloromethane (100 mL). The aqueous layer was washed with dichloromethane (3×100 mL) and then water was removed via rotary evaporator followed by hi-vac to yield a very dark solid (20.75 g). The dark solid was chromatographed on AG 50W X8 (hydrogen form, 100 g) cation exchange resin using 1N HCl followed by 2N HCl as the eluent system. The progress of the separation was monitored by taking aliquots directly from the column, placed directly into an NMR tube without lock solvent, and checking each aliquot for the appearance of a $^{13}$C signal by running an unlocked NMR experiment. Once a signal appeared, authentic urea-$^{13}$C ($\delta$=163 ppm) was added as a standard for comparison. Urea-13C co-eluted with ammonium chloride as the first fraction, which was eluted using 1N HCl. The eluent was changed to 2N HCl once the signal for urea-$^{13}$C disappeared. Guanidine-$^{13}$C hydrochloride ($\delta$=158 ppm) appeared as the second fraction. The aqueous acid was removed from the fractions first using a rotary evaporator, and then dried using hi-vac with a nitrogen trap. The first fraction was then washed with cold ethanol and filtered to remove the ammonium chloride. The ethanol was removed using rotary evaporator followed by hi-vac to give urea-$^{13}$C as a very pale yellowish solid (2.9 g, 0.047 mol, 49%). The second fraction gave guanidine-$^{13}$C hydrochloride as a pale tan solid (4.3 g, 0.0446 mol, 47%) which was used without further purification.

The spectra data are as follows:
$^1$H NMR (D$_2$O, 300 MHz): $\delta$=NA
$^{13}$C NMR (D$_2$O, 75 MHz): $\delta$=158.

Synthesis of Synthesis of 1-[(phenylthio)[$^{13}$C]methyl]-2,5-Pyrrolidinedione

Succinimide (0.74 g, 0.0075 moles) was dissolved ethanol (8 mL) which contained sodium hydroxide (0.30 g, 0.0075 moles). This solution was stirred for 30 minutes and then the ethanol was removed by evaporation. To the resulting solid was suspended into acetonitrile (15 mL). To this mixture chloro[$^{13}$C]methyl phenyl sulfide (1.19 g, 0.0075 moles) and the reaction was stirred at room temperature until complete. After 3 days the reaction was worked-up by the addition of water followed by extraction with dichloromethane (3×50 mL). The organic layer was dried over sodium sulfate, evaporated in vacuo to give the crude product. The product was purified by column chromatography.

The spectra data are as follows:
$^1$HNMR (300 MHz in CDCl$_3$ with 0.03% TMS)/$\delta$: 7.49-7.26 (m 5H), $\delta$: 4.83 (d, J=155.49 $^{13}$CH$_2$, 2H); $\delta$: 2.65 (s, C H$_2$CH$_2$, 4H)
$^{13}$CNMR (75 MHz in CDCl$_3$) $\delta$: 136.0, 132.43, 129.32, 128.14 $\delta$: 86.43, 42.39 (s, $^{13}$CH$_2$) $\delta$: 28.19, (CH$_2$CH$_2$).

The embodiments of the invention in which an exclusive property or right is claimed are defined as follows.

Having thus described the invention what is claimed is:

1. A population of a labeled compound having the structure:

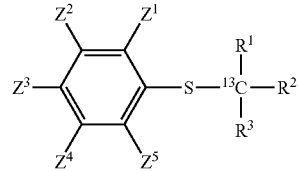

wherein $Z^1$ is H;
wherein $Z^2$ is H;
wherein $Z^3$ is H;
wherein $Z^4$ is H;
wherein $Z^5$ is H;
wherein $R^1$ is H;
wherein $R^2$ is H;
wherein $R^3$ is —O-alkyl; and
wherein the population isotopically enriched.

* * * * *